United States Patent
Numata

(10) Patent No.: US 7,331,249 B2
(45) Date of Patent: Feb. 19, 2008

(54) NON-DESTRUCTIVE INSPECTION APPARATUS AND NON-DESTRUCTIVE INSPECTION SYSTEM

(75) Inventor: Kenji Numata, Tokyo (JP)

(73) Assignee: Olympus Corporation, Tokyo (JP)

( * ) Notice: Subject to any disclaimer, the term of this patent is extended or adjusted under 35 U.S.C. 154(b) by 59 days.

(21) Appl. No.: 11/294,920

(22) Filed: Dec. 6, 2005

(65) Prior Publication Data
US 2006/0265094 A1 Nov. 23, 2006

(30) Foreign Application Priority Data
Dec. 8, 2004 (JP) ............ P2004-355630
Nov. 29, 2005 (JP) ............ P2005-343764

(51) Int. Cl.
*G01M 19/00* (2006.01)
(52) U.S. Cl. .................................... 73/865.8
(58) Field of Classification Search ........... 73/865.8, 73/598, 592, 632, 628, 625, 622, 624, 641
See application file for complete search history.

(56) References Cited

U.S. PATENT DOCUMENTS

| | | | | | |
|---|---|---|---|---|---|
| 4,055,989 | A | * | 11/1977 | Henry et al. .............. | 73/588 |
| 4,365,514 | A | * | 12/1982 | Ho ........................ | 73/592 |
| 5,675,506 | A | * | 10/1997 | Savic ..................... | 702/51 |
| 6,016,700 | A | * | 1/2000 | Cuffe ..................... | 73/602 |
| 2002/0154811 | A1 | * | 10/2002 | Katsuta et al. ............ | 382/151 |
| 2004/0261547 | A1 | * | 12/2004 | Russell et al. ............ | 73/865.8 |
| 2006/0010979 | A1 | * | 1/2006 | Sakai et al. .............. | 73/598 |

FOREIGN PATENT DOCUMENTS

| | | |
|---|---|---|
| JP | 7-155290 | 6/1995 |
| JP | 2002-22713 | 1/2002 |
| JP | 2002022713 A * | 1/2002 |

* cited by examiner

*Primary Examiner*—Hezron Williams
*Assistant Examiner*—John Fitzgerald
(74) *Attorney, Agent, or Firm*—Scully, Scott, Murphy & Presser, P.C.

(57) ABSTRACT

A nondestructive inspection device nondestructively inspects an internal state of an inspection target, and transmits information indicating a progress status of the inspection to the outside of an inspection site. A nondestructive inspection system which uses this nondestructive inspection device includes a network connected to the nondestructive inspection device, and one or a plurality of computers connected via the network to the nondestructive inspection device.

6 Claims, 7 Drawing Sheets

FIG. 5

207 — DISPLAY AREA: LEFT MAIN WING SECTION OF JET NO. 2
208 — INSPECTION PERIOD: 2004.09.02 TO PRESENT
209 — INSPECTION HISTORY OF BLOCK AC: 2004.09.02 FAIL
　　　　　　　　　　　　　　　　　　　　2004.06.08 PASS
　　　　　　　　　　　　　　　　　　　　2004.02.20 PASS

206 — DETAILS / DETAILS / DETAILS

202 — UNINSPECTED
203 — INSPECTION UNDERWAY
204 — PASS
205 — FAIL

201 —

| CA | CB | CC | CD | CE |    |    |    |
| BA | BB | BC | BD | BE | BF | BG |    |
| AA | AB | AC | AD | AE | AF | AG | AH |

DETAILS OF FAILURE OF BLOCK AC

INSPECTION DATA 301

302 — INSPECTION DATE AND TIME: 2004.09.02 11:20
303 — POSITION OF FAILED PART: X = 100 MM, Y = 20 MM FROM STARTING POINT
304 — INSPECTION DEVICE USED: ULTRASONIC INSPECTION DEVICE A1
305 — INSPECTION DEVICE SETTING INFORMATION:
   GAUGE80dB
   RANGE50mm
   FREQUENCY10MHz
   VOLTAGE150V
   . . . .

US 7,331,249 B2

NON-DESTRUCTIVE INSPECTION APPARATUS AND NON-DESTRUCTIVE INSPECTION SYSTEM

BACKGROUND OF THE INVENTION

Priority is claimed on Japanese Patent Application No. 2004-355630, filed Dec. 8, 2004, the content of which is incorporated herein by reference.

1. Field of the Invention

The present invention relates to a nondestructive inspection device and a nondestructive inspection system.

2. Description of Related Art

A nondestructive inspection device inspects the internal state of an inspection target without destroying it. Recently, nondestructive inspection devices are widely used in industrial fields, such as in inspections of airplane fuselages and equipment at large-scale industrial plants. Such nondestructive inspection devices use ultrasonic waves, eddy current, acoustic inspection, radiation of rays such as X-rays, and thermography.

For example, Japanese Unexamined Patent Application, First Publication No. 2002-22713 discloses an ultrasonic flaw-detection system in which a control terminal device installed at a remote inspection site is connected via a network to a server installed at a center. The control terminal device transmits flaw-detection data obtained from an ultrasonic flaw-detection device for ultrasonic flaw-detection via the network to the server in real time. The server analyzes and evaluates the flaw-detection data it receives from the control terminal device. This ultrasonic flaw-detection system also includes a terminal device which can access the server via the network and evaluate the analysis of the flaw-detection data made by the server.

SUMMARY OF THE INVENTION

A nondestructive inspection device of the present invention nondestructively inspects an internal state of an inspection target and transmits information indicating a progress status of the inspection to the outside.

In addition to the information indicating the progress status of the inspection, the nondestructive inspection device may also transmit information indicating an inspection result of the nondestructive inspection to the outside.

In addition to the information indicating the progress status of the inspection, the nondestructive inspection device may also transmit inspector information indicating an inspector who carries out the nondestructive inspection to the outside.

The nondestructive inspection device may transmit both or one of information indicating the progress status of the nondestructive inspection and information indicating the inspection result for each block which is set in the nondestructive inspection target to the outside.

When the inspection result is a failure, the nondestructive inspection device may transmit positional data relating to a failed part of the inspection target and inspection data relating to the failed part to the outside.

A nondestructive inspection system of the present invention comprises the nondestructive inspection device described above, a network which is connected to the nondestructive inspection device, and one or a plurality of computers which is/are connected via the network to the nondestructive inspection device.

In this nondestructive inspection system, one of the plurality of computers may be a server computer, and the other, a client computer. The nondestructive inspection device transmits information indicating the progress status of the inspection to the server computer, and the server computer supplies this information to the client computer.

BRIEF DESCRIPTION OF THE DRAWINGS

FIG. 5 is a schematic diagram showing an example of a display of nondestructive inspection information obtained from the nondestructive inspection system according to the embodiment of the present invention;

DETAILED DESCRIPTION OF THE INVENTION

An embodiment of the present invention will be explained with reference to the drawings. While by way of example, the embodiment describes a nondestructive inspection device and a nondestructive inspection system which use ultrasonic waves execute a nondestructive inspection of an airplane (target), the present invention can be applied in a nondestructive inspection system which executes a nondestructive inspection of the target using a method other than ultrasonic waves, e.g. eddy current, acoustic inspection, radiation of waves such as X-rays, and thermography.

Figure 1:
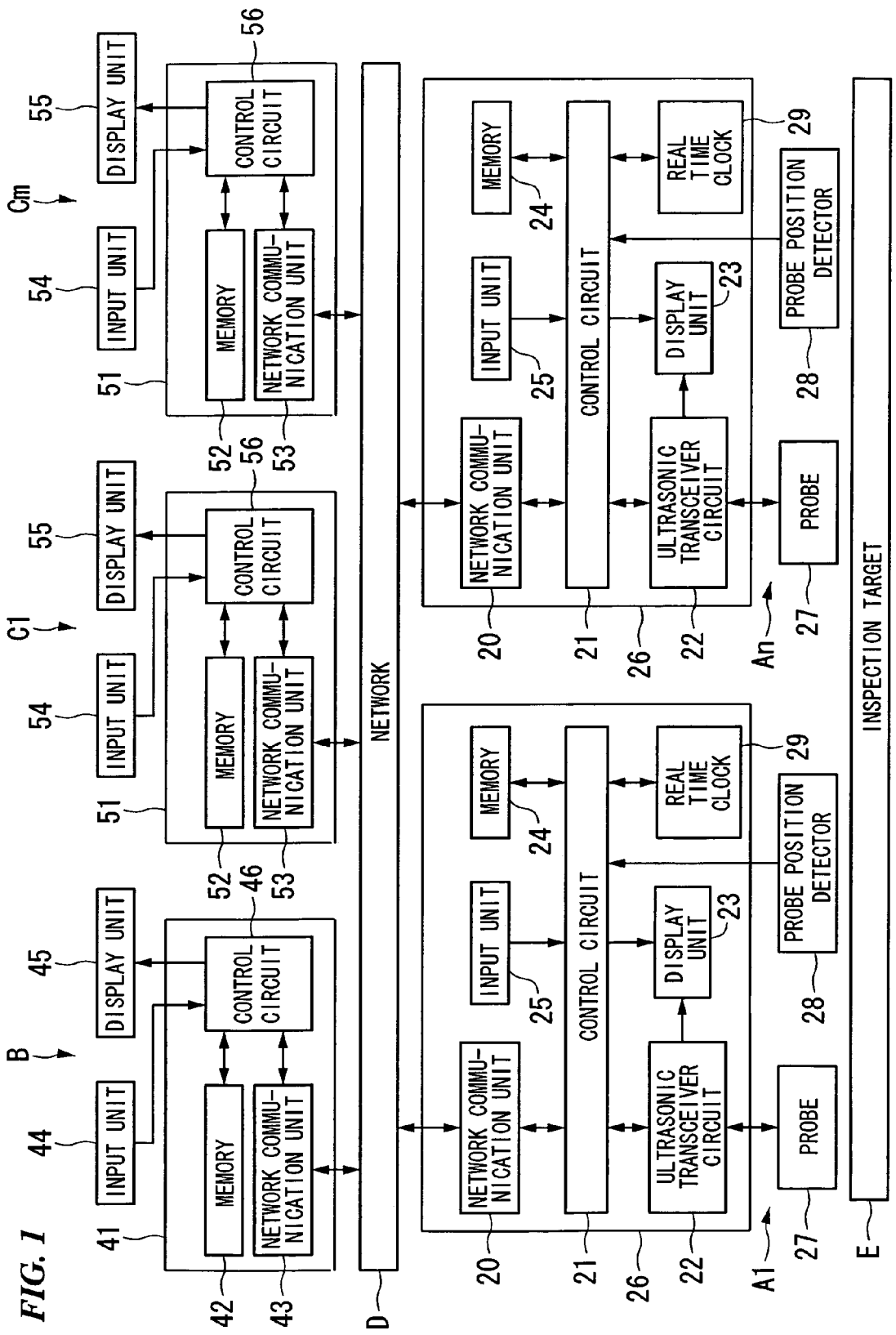
FIG. 1 is a block diagram showing a nondestructive inspection system according to an embodiment of the present invention.

FIG. 1 is a block diagram of the functional configurations of a nondestructive inspection device and a nondestructive inspection system according to this embodiment. As shown in FIG. 1, this nondestructive inspection system includes a plurality of ultrasonic inspection devices A1 to An (nondestructive inspection devices), a plurality of client computers C1 to Cm which are connected via a network D to the ultrasonic inspection devices A1 to An, and a server computer B which is similarly connected. In the following explanation, the client computers C1 to Cm will simply be termed "clients C1 to Cm", and the server computer, "server B".

Each of the ultrasonic inspection devices A1 to An comprises an ultrasonic inspection device main unit 26 which includes a network communication unit 20, a control circuit 21, an ultrasonic transceiver circuit 22, a display unit 23 such as an LCD or a CRT, a memory 24, an input unit 25 consisting of buttons, a touch panel, a rotary encoder, and the like, and a real time clock 29 which has a clock function. The ultrasonic inspection devices A1 to An also include a probe 27 and a probe position detector 28, which are connected to the ultrasonic inspection device main unit 26. The network communication unit 20 connects to the control circuit 21 and the network D. The ultrasonic transceiver circuit 22 connects to the display unit 23 and the probe 27. The display unit 23, the memory 24, the input unit 25, and the real time clock 29 connect to the control circuit 21.

The server B has a server main unit 41 which includes a network communication unit 43, a memory 42, and a control circuit 46. The server B also includes a display unit 45, such as an LCD or a CRT, and an input unit 44 consisting of a keyboard, a mouse, and the like; these are connected to the server main unit 41. The network communication unit 43 is connected to the control circuit 46 and the network D. The memory 42, the display unit 45, and the input unit 44, each connect to the control circuit 46. The server B sequentially receives nondestructive inspection information relating to an airplane from the ultrasonic inspection devices A1 to An via the network D, and sequentially stores this information in the memory 42. In response to requests from the clients C1 to Cm, the server B supplies the nondestructive inspection information in the memory 42 to the clients C1 to Cm via the network D.

Each of the clients C1 to Cm comprises a PC main unit 51 which includes a network communication unit 53, a memory 52, and a control circuit 56, an input unit 54 including a keyboard, a mouse, and the like, and a display unit 55 such as an LCD or a CRT. The network communication unit 53 connects to the control circuit 56 and the network D. The memory 52, the display unit 55, and the input unit 54 each connect to the control circuit 56. The clients C1 to Cm access the server B via the network D and obtain the nondestructive inspection information relating to the airplane which is accumulated in the server B. A LAN, a wireless LAN, a wired telephone line, a mobile telephone line, or the like, is used as the network D.

Figure 2:
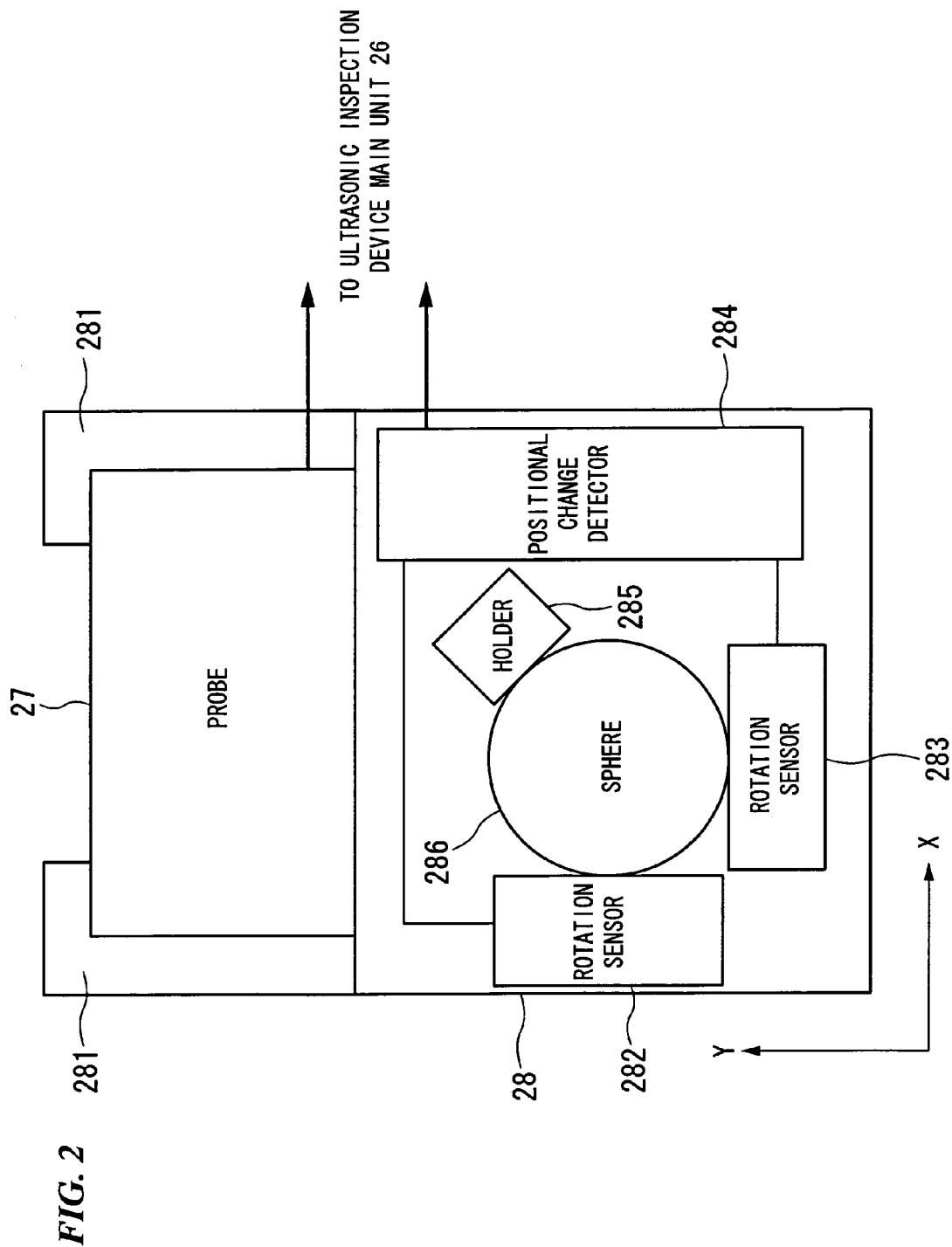
FIG. 2 is a diagram showing a probe position detector in the nondestructive inspection system according to the embodiment of the present invention.

FIG. 2 is a diagram of the detailed configuration of the probe position detector 28. The probe position detector 28 comprises a probe holder 281 which holds a probe 27, a sphere 286, a rotation sensor 282 which detects the X-directional rotation of the sphere 286, a rotation sensor 283 which detects the Y-directional rotation of the sphere 286, a positional change detector 284 which is connected to the sensors 282 and 283, and a sphere holder 285 which holds the sphere 286 at an appropriate position. When the probe position detector 28 is moved while pressing the probe 27 against the inspection target, the sphere 286 rotates in the direction that the probe position detector 28 moves in. The probe position detector 28 detects the position (X-Y coordinates) of the probe 27 held by the probe holder 281 by using the rotation sensors 282 and 293 to detect the rotation of the sphere 286.

Figure 3:
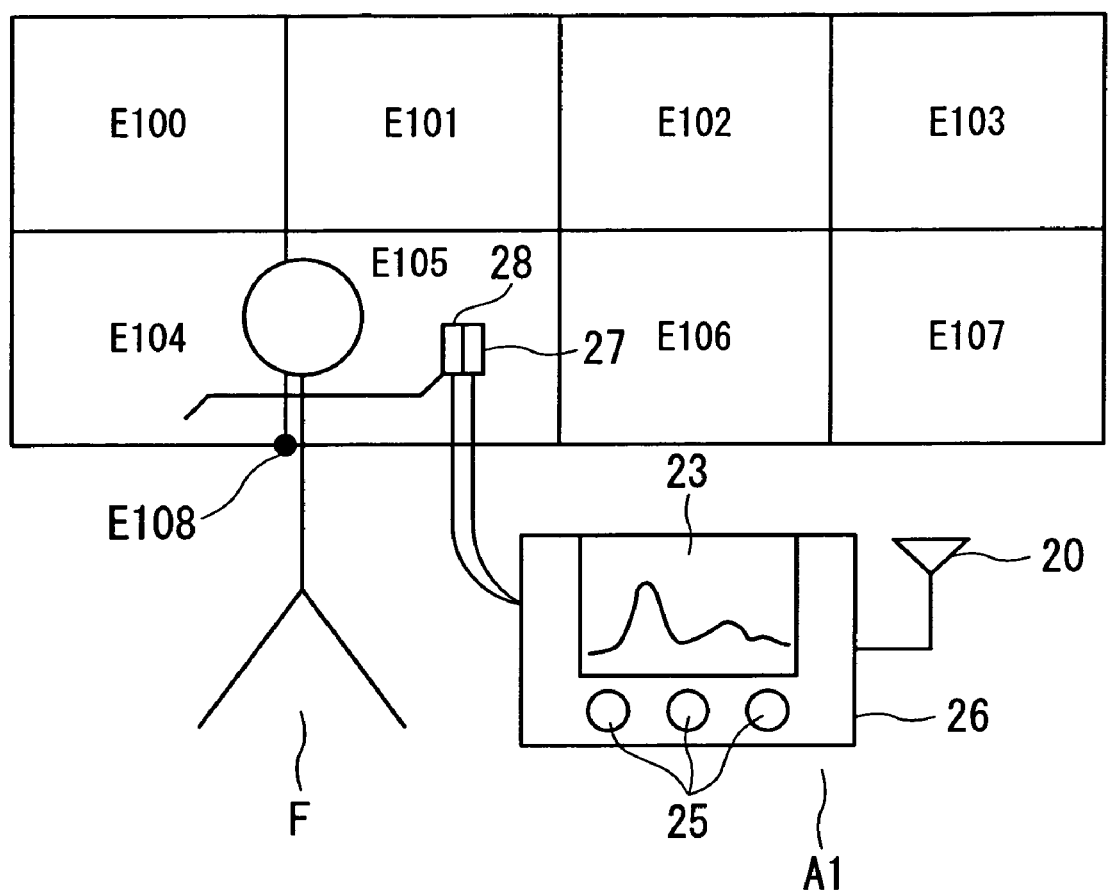
FIG. 3 is a schematic diagram showing an inspection of an airplane using the nondestructive inspection system according to the embodiment of the present invention.

FIG. 3 is a schematic diagram of an airplane being inspected using the ultrasonic detection device. While for sake of convenience, FIG. 3 depicts only one ultrasonic inspection device A1, an actual inspection usually uses a plurality of the ultrasonic inspection devices A1 to An to simultaneously inspect an inspection target E of an airplane (e.g. a fuselage, a jet engine). During an inspection using the ultrasonic inspection device A1, the inspection target E is divided as appropriate beforehand into blocks E100 to E107. An inspector F performs the inspection by pressing the probe 27 against each of the blocks E100 to E107.

For example, the block E105 is inspected by sequentially moving the probe 27 from a starting point E108 through all regions of the block E105. Reflected-wave detection signals from the probe 27 are sequentially supplied to the ultrasonic inspection device main unit 26. In addition, the probe position detector 28 sequentially detects the position of the probe 27 and supplies it to the ultrasonic inspection device main unit 26. As a result, the detection result for each position of the probe 27 is displayed on the display unit 23 and transmitted via the network communication unit 20 to the network D.

Figure 4:
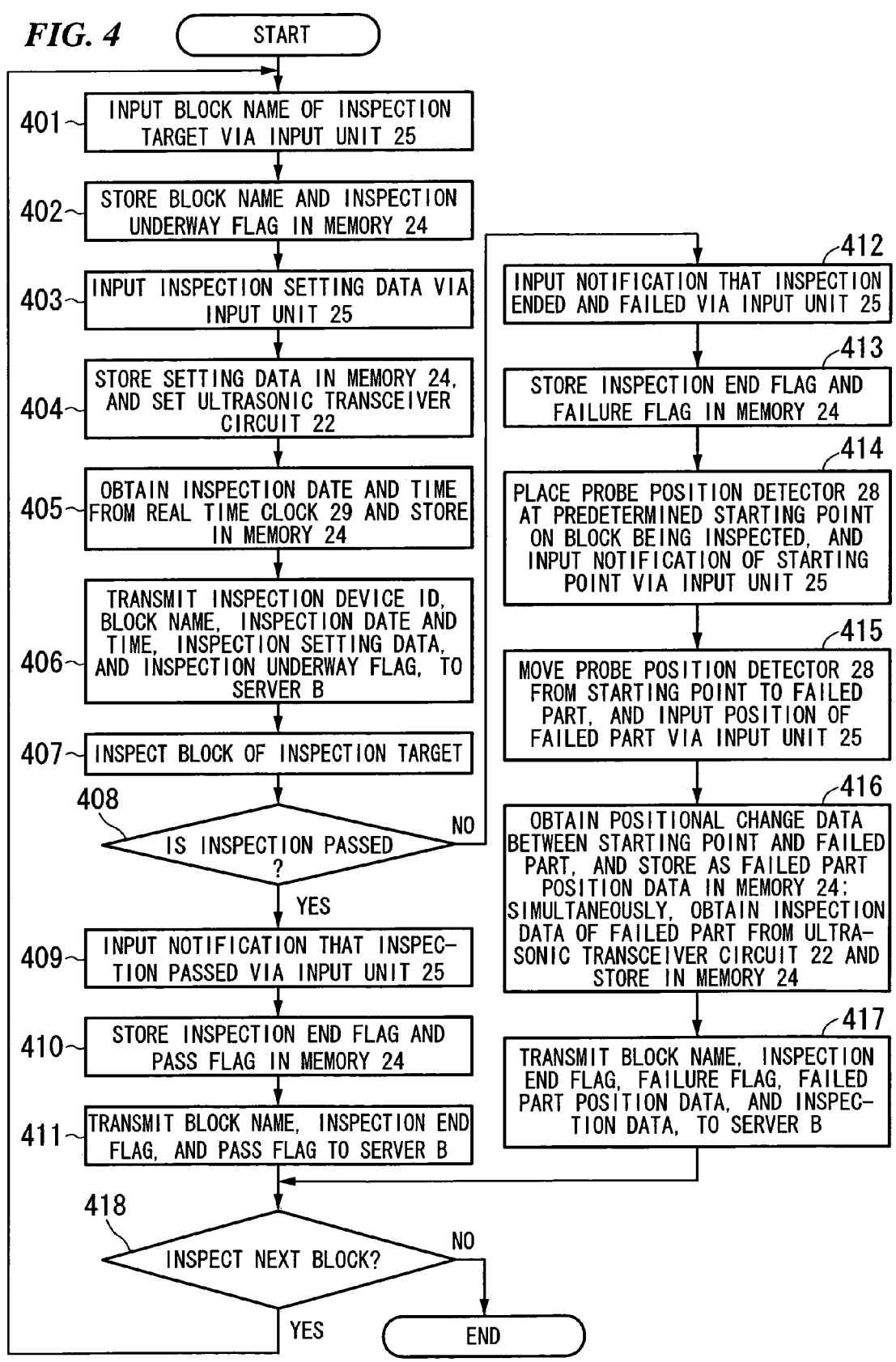
FIG. 4 is a flowchart showing an inspection procedure using the nondestructive inspection system according to the embodiment of the present invention.

Subsequently, an operation (i.e. an inspection procedure) of the nondestructive inspection system configured as above will be explained in detail based on the flowchart of FIG. 4.

Using the input unit 25, the inspector F inputs a name of the block of the inspection target E which is to be inspected to the control circuit 21 (step 401). The control circuit 21 stores the block name obtained from the input unit 25, and an inspection underway flag which indicates that an inspection is currently underway, in the memory 24 (step 402). The inspector F then inputs inspection setting data for executing a most appropriate ultrasonic inspection of the inspection target E to the control circuit 21 by operating the input unit 25 (step 403). The control circuit 21 stores the inspection setting data in the memory 24 and sets the ultrasonic transceiver circuit 22 in accordance therewith (step 404).

The control circuit 21 obtains the present date and time from the real time clock 29 and stores it in the memory 24 as an inspection date and time (step 405). The control circuit 21 then supplies an inspection device ID, the block name, the inspection date and time, the inspection setting data, and the inspection underway flag, which are stored in the memory 24, to the network communication unit 20 for transmission to the server B (step 406). Based on a transmission command from the control circuit 21, the network communication unit 20 transmits the above information via the network D to the server B.

The inspector F inspects the block which constitutes the inspection target by moving the probe 27 (step 407). During the inspection, the control circuit 21 controls the ultrasonic transceiver circuit 22 based on the inspection setting data such that the ultrasonic transceiver circuit 22 outputs a high-voltage pulse to the probe 27, which transmits an ultrasonic signal toward the inspection target E. The ultrasonic signal is reflected within the inspection target E, and the reflected-wave signal is received by the ultrasonic transceiver circuit 22 via the probe 27. The ultrasonic transceiver circuit 22 signal-processes the reflected-wave signal and displays it in waveform format as an inspection result on the display unit 23.

Based on the reflected-wave signal displayed on the display unit 23, the inspector F determines whether the inspection target E has passed/failed by evaluating whether it has any defects such as blemishes (step 408). When it passes the inspection, the inspector F operates the input unit 25 to input a determination result of "Pass" to the control circuit 21 (step 409). The control circuit 21 stores an inspection end flag, which indicates that the inspection has ended, and a pass flag, which indicates that the inspection target E passed the inspection, in the memory 24 (step 410). The control circuit 21 then supplies the block name of the target, the inspection end flag, and the pass flag to the network communication unit 20 and transmits them to the server B (step 411). As a result, the inspection end flag and the pass flag relating to the block name of the inspection target are stored together in the server B.

On the other hand, when the inspector F determines that the inspection target E has failed, he inputs this failure to the control circuit 21 by manipulating the input unit 25 (step 412). The control circuit 21 stores the inspection end flag, which indicates that the inspection has ended, and a failure flag which indicates that the inspection target has failed the inspection, to the memory 24 (step 413).

The inspector F places the probe 27 at a predetermined starting point on the block which constitutes the inspection target, and inputs notification that the probe 27 is at the starting point to the control circuit 21 by further manipulating the input unit 25 (step 414). The inspector F then moves the probe 27 from the starting point to a failed part, and inputs notification that the probe 27 is at the failed part to the control circuit 21 by further manipulating the input unit 25 (step 415).

As a result, the control circuit 21 obtains positional change data from the starting point to the failed part from the probe position detector 28, and stores it as failure position data in the memory 24. At the same time, the control circuit 21 obtains inspection data of the failed part from the ultrasonic transceiver circuit 22 and stores it in the memory 24 (step 416). Thereafter, the control circuit 21 transmits the block name, the inspection end flag, the failure flag, the failure position data, and the inspection data from the network communication unit 20 to the server B (step 417).

To inspect the next block, the inspector F returns to step 401 and inspects the next block (step 418). If he does not inspect the next block, the inspection ends at this point.

When the ultrasonic inspection devices A1 to An are inspected without being connected to the network D, the control circuit 21 of each of the ultrasonic inspection devices A1 to An transmits the above types of information to the server B after detecting that the network communication unit 20 has been connected to the network D.

By these inspections using the ultrasonic inspection devices A1 to An, the server B receives nondestructive inspection data relating to the airplane from the ultrasonic inspection devices A1 to An via the network D and sequentially accumulates them in each block. That is, the control circuit 46 of the server B sequentially stores nondestructive inspection information, such as the inspection result of each block (pass flag or failure flag), a progress status of the inspection (inspection underway flag or inspection end flag), the date and time of the inspection, the inspection device ID, the inspection setting data, the failure position data, the inspection data, which are sequentially received from the ultrasonic inspection devices A1 to An via the network D, in the memory 42.

The control circuit 46 displays the nondestructive inspection information of each block of the inspection target E stored in the memory 42 on the display unit 45. When a command to change the display contents is input from the input unit 44, the control circuit 46 changes the display contents by controlling the display unit 45. When the network communication unit 43 receives requests to browse the nondestructive inspection information from the network communication units 53 of the clients C1 to Cm, the control circuit 46 responds to these request by supplying that information to the clients C1 to Cm via the network D.

Figure 6:
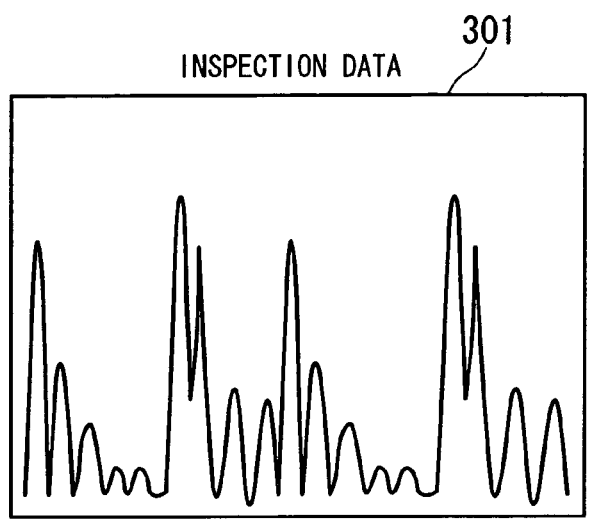
FIG. 6 is a schematic diagram showing another example of a display of nondestructive inspection information obtained from the nondestructive inspection system according to the embodiment of the present invention.

FIGS. 5 and 6 are schematic diagrams of display examples of nondestructive inspection information displayed on the display unit 45 of the server B or the display units 55 of the clients C1 to Cm. In FIG. 5 inspection results and inspection progress statuses of all the blocks are displayed as schematic diagrams 201a for a display area 207 and an inspection period 208, which are selected via the input unit 44 of the server B or the input units 54 of the clients C1 to Cm. In FIG. 5, a display represented by reference numeral 202 represents "Uninspected", 203 represents "Inspection Underway", 204 represents "Pass Inspection", and 205 represents "Failed Inspection". This type of display method makes it easy for the server B or the clients C1 to Cm to visually ascertain not only the inspection result of each block but also the progress of the inspections.

The schematic diagram 201 depicts "Left Main Wing Section of Jet" selected in a display area 207. Alternatively, it would be acceptable to draw the blocks on a photograph of the actual object or a cubic diagram using a three-dimensional CAD which is more precise and more closely resembles the actual object, and display the inspection results and progress statuses of the inspections in separate blocks.

When, for example, a failed block AC in the schematic diagram 201 is selected by manipulating the input unit 44 or the input unit 54, the control circuit 46 displays an inspection history 209 of the block AC on the display unit 45 or the display unit 55. When detailed information 206 relating to the block AC is selected by manipulating the input unit 44 or the input unit 54, the control circuit 46 displays detailed information such as that shown in FIG. 6, including an inspection date and time 302, an inspection device ID 304, inspection device setting information 305 which constitutes the inspection setting data, a failure position 303, inspection data 301, and so on, in the display unit 45 or the display unit 55.

The present invention is not limited to the embodiment described above and can be modified in various ways such as the following.

(1) The control circuits 21 of the ultrasonic inspection devices A1 to An may transmit the reflected signal received by the ultrasonic transceiver circuit 22 and the positional data of the probe 27 obtained by the probe position detector 28 via the network D to the server B or the clients C1 to Cm by controlling the network communication unit 20. In this case, the inspection is evaluated and determined as pass/fail on the server B side or the clients C1 to Cm side.

(2) The control circuit 46 of the server B may control the network communication unit 43 such as to transmit an inspection procedure, an inspection item list, inspection setting data of the ultrasonic inspection devices A1 to An, and other commands, to the ultrasonic inspection devices A1 to An in accordance with the statuses of the inspections. Alternatively, the control circuits 21 of the ultrasonic inspection devices A1 to An may control the network communication units 20 such as to transmit an inspection manual, an inspection procedure, an inspection item list, and inspection setting data of the ultrasonic inspection devices A1 to An in accordance with the inspection statuses from the server B.

Figure 7:
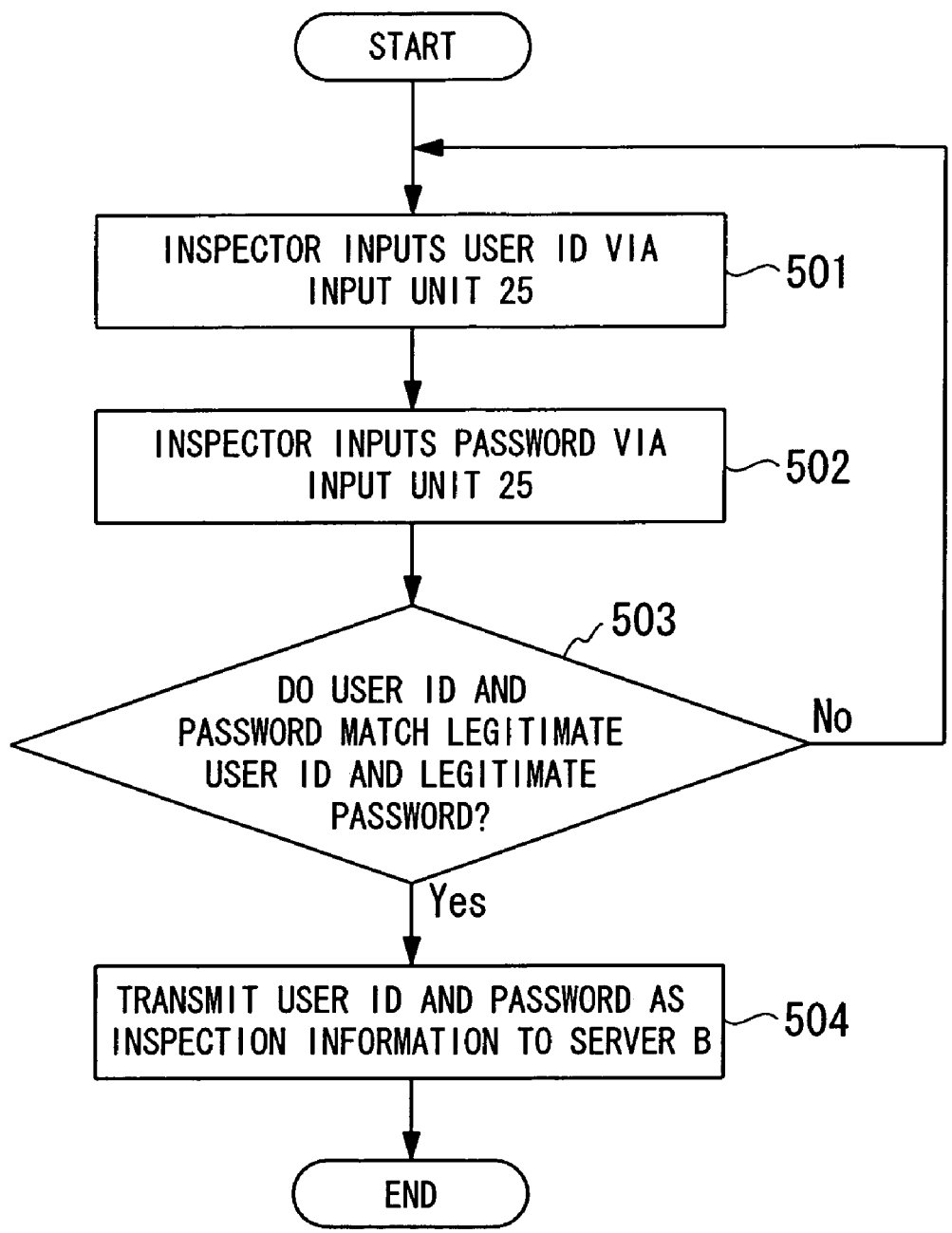
FIG. 7 is a flowchart showing a process of authenticating an inspector in the nondestructive inspection system according to the embodiment of the present invention.

In addition to the progress status of the inspection and the inspection result mentioned above, an authentication process shown in FIG. 7 may be executed as preprocessing for the process shown above in FIG. 4 in order to transmit inspector information for identifying the inspector from the ultrasonic inspection devices A1 to An to the server B.

That is, after the inspector turns on the power of the ultrasonic inspection devices A1 to An by manipulating the input unit 25, he inputs his user ID (step 501) and his password (step 502) by further manipulating the input unit 25. An inspector user ID (legitimate user ID) and a password (legitimate password) are stored beforehand in the memories 24 of the ultrasonic inspection devices A1 to An. The control circuit 21 compares the user ID and the password input from the input unit 25 with the legitimate user ID and the legitimate password stored in each memory 24, and, if they match (step 503), determines that the inspector is the legitimate inspector. In this case, the control circuit 21 permits the inspector to use the ultrasonic inspection devices A1 to An, and permits him to proceed to the inspection shown in FIG. 4.

The control circuit 46 of the server main unit 41 controls the network communication unit 20 such that the authenticated user ID and password of the inspector are transmitted to the server B as inspector information (step 504).

The user ID and the password are authenticated in this way every time use of the ultrasonic inspection devices A1 to An starts, and the authenticated user ID and the password are transmitted from the ultrasonic inspection devices A1 to An to the server B. This enables the user (i.e. the inspector) of the ultrasonic inspection devices A1 to An to be identified, ensuring that an accurate inspection history is obtained.

As described above according to the nondestructive inspection device of the present invention, since information indicating the progress status of the inspection is transmitted to the outside, it becomes easier to ascertain the status of the inspection of the inspection target at an inspection site in real time at a location other than the inspection site.

According to the abovementioned embodiment of the nondestructive inspection device, in addition to the status of the inspection of the inspection target at an inspection site, it is also possible to ascertain the inspection result in real time at a location other than the inspection site.

According to the abovementioned embodiment of the nondestructive inspection device, in addition to the status of the inspection of the inspection target at an inspection site, it is also possible to identify the inspector who carries out the inspection at a location other than the inspection site. This enables the inspection history and the like to be ascertained more accurately.

According to the abovementioned embodiment of the nondestructive inspection device, the status of the inspection of the inspection target at an inspection site and the inspection result can be ascertained easily and in real time in each of the blocks which are set in the inspection target, at a location other than the inspection site.

Moreover according to the abovementioned embodiment of the nondestructive inspection device, positional data relating to a failed part of the inspection target and inspection data relating to the failed part can be ascertained easily and in real time at a location other than the inspection site.

According to the nondestructive inspection system of this invention, the progress status of the inspection by the nondestructive inspection device at the inspection site and an inspection result thereof can be ascertained easily and in real time by a computer which is connected to the nondestructive inspection device via a network and installed at a location other than the inspection site.

Moreover according to the abovementioned embodiment of the nondestructive inspection system, the progress status of the inspection by the nondestructive inspection device at the inspection site and the inspection result thereof are sequentially accumulated in a server computer. This enables a client computer, which is installed at a location other than the inspection site, to ascertain the inspection history by accessing the server computer.

What is claimed is:

1. An inspection system comprising:
an inspection device comprising:
an inspection information receiving unit which receives inspection information for each block of a plurality of blocks set in an inspection target:
a first memory which stores, corresponding to each of the blocks, a block name of the block from which the inspection information is received by the inspection information receiving unit, a pass flag indicating that the inspection information received from the block show absence of defect in the block, and a failure flag indicating that the inspection information received from the block show presence of defect in the block: and
a communication unit which transmits to the outside the block name, the pass flag and the failure flag stored in the first memory corresponding to each of the blocks: and
a computer comprising:
a second memory which stores, corresponding to each of the blocks, the block name, the pass flag and the failure flag transmitted from the first memory: and
a display unit which has a display area corresponding to the inspection target and including a plurality of display blocks arranged to be associated with each of the blocks, the display unit displaying in the associated display block discrimination to indicate whether the result of the inspection is passed or failed based on the block name, the pass flag and the failure flag stored in the second memory.

2. The inspection system according to claim 1, wherein:
the first and second memories further stores, corresponding to each of the blocks, an inspection underway flag indicating that an inspection is currently underway by the inspection information receiving unit; and
the display unit further displays in the associated display block discrimination to indicate whether or not the associated block is in a inspection underway condition based on the inspection under way flag stored in the second memory.

3. The inspection system according to claim 1, wherein:
a plurality of the inspection devices are connected to the computer;
the first and second memories further stores an inspection device ID assigned to each of the inspection devices for identifying one of the inspection devices; and
the display unit further displays the inspection device ID stored in the second memory.

4. The inspection system according to claim 1, wherein:
the first and second memories further stores, corresponding to each of the blocks, an inspection data obtained by the inspection information receiving unit; and
the display unit further displays in the associated display block the inspection data stored in the second memory.

5. The inspection system according to claim 1, wherein:
the first and second memories further stores inspector information assigned to each of inspectors for indicating an inspector who carries out the inspection of the inspection target; and
the display unit further displays the inspector information stored in the second memory.

6. The inspection system according to claim 1, wherein:
the display unit displays a photograph or a cubic diagram of the inspection target in the display area; and
the display blocks are provided on the photograph or the cubic diagram.

* * * * *